US009999404B2

(12) United States Patent
Kato et al.

(10) Patent No.: US 9,999,404 B2
(45) Date of Patent: Jun. 19, 2018

(54) ULTRASONIC DIAGNOSTIC APPARATUS

(71) Applicant: GE Medical Systems Global Technology Company, LLC, Waukesha, WI (US)

(72) Inventors: Sei Kato, Tokyo (JP); Hiroshi Hashimoto, Tokyo (JP)

(73) Assignee: General Electric Company, Schenectady, NY (US)

(*) Notice: Subject to any disclaimer, the term of this patent is extended or adjusted under 35 U.S.C. 154(b) by 303 days.

(21) Appl. No.: 14/725,444

(22) Filed: May 29, 2015

(65) Prior Publication Data

US 2015/0342568 A1 Dec. 3, 2015

(30) Foreign Application Priority Data

May 29, 2014 (JP) ................. 2014-111064

(51) Int. Cl.
*A61B 8/08* (2006.01)
*A61B 8/00* (2006.01)
(Continued)

(52) U.S. Cl.
CPC .............. *A61B 8/5207* (2013.01); *A61B 8/14* (2013.01); *A61B 8/4254* (2013.01);
(Continued)

(58) Field of Classification Search
CPC ....... A61B 8/5207; A61B 8/4444; A61B 8/54; A61B 8/14; A61B 8/4254; A61B 8/461;
(Continued)

(56) References Cited

U.S. PATENT DOCUMENTS 4,989,143 A 1/1991 O'Donnell et al.
5,415,173 A * 5/1995 Miwa ................. G01S 7/52049
600/447

(Continued)

FOREIGN PATENT DOCUMENTS

JP 59212791 A 12/1984
JP 04117954 A 4/1992
(Continued)

OTHER PUBLICATIONS

Yoon et al., Optimal Sound Speed Estimation Using Modified Nonlinear Anisotropic Diffusion to Improve Spatial Resolution in Ultrasound Imaging, IEEE Transactions on Ultrasonics, Ferroelectrics, and Frequency Control, vol. 59, No. 5, May 2012.*

(Continued)

*Primary Examiner* — Bo J Peng

(57) ABSTRACT

An ultrasonic diagnostic apparatus is characterized in comprising: an ultrasonic probe for transmitting/receiving ultrasound to/from a subject; a reception beamformer for applying reception beamforming to ultrasonic echo signals obtained by the ultrasonic probe based on a plurality of different sound velocities; a spatial frequency analyzing section 81 for applying spatial frequency analysis to each of data obtained by the reception beamforming based on each of the plurality of different sound velocities; and a sound-velocity setting section 84 for setting a sound velocity corresponding to one of the results of spatial frequency analysis corresponding respectively to the plurality of different sound velocities that has a highest intensity for a given spatial frequency, as optimal sound velocity in the reception beamforming.

11 Claims, 14 Drawing Sheets

(51) Int. Cl.
*A61B 8/14* (2006.01)
*G01S 7/52* (2006.01)
*G10K 11/34* (2006.01)

(52) U.S. Cl.
CPC ............ *A61B 8/4444* (2013.01); *A61B 8/461* (2013.01); *A61B 8/469* (2013.01); *A61B 8/5269* (2013.01); *A61B 8/54* (2013.01); *G01S 7/52049* (2013.01); *G10K 11/346* (2013.01)

(58) Field of Classification Search
CPC .... A61B 8/5269; A61B 8/469; G10K 11/346; G01S 7/52049
See application file for complete search history.

(56) References Cited

U.S. PATENT DOCUMENTS

| | | | |
|---|---|---|---|
| 6,322,505 B1 * | 11/2001 | Hossack | A61B 8/00 |
| | | | 600/437 |
| 8,372,008 B2 | 2/2013 | Katsuyama | |
| 8,708,910 B2 | 4/2014 | Katsuyama | |
| 8,926,512 B2 | 1/2015 | Kakee | |
| 2004/0073112 A1 * | 4/2004 | Azuma | A61B 8/08 |
| | | | 600/437 |
| 2005/0043622 A1 * | 2/2005 | Jensen | G01S 7/52085 |
| | | | 600/449 |
| 2006/0184023 A1 * | 8/2006 | Satoh | A61B 8/14 |
| | | | 600/437 |
| 2009/0204003 A1 * | 8/2009 | Guracar | A61B 8/06 |
| | | | 600/458 |
| 2010/0076312 A1 * | 3/2010 | Katsuyama | A61B 8/00 |
| | | | 600/443 |
| 2011/0077519 A1 | 3/2011 | Katsuyama | |

FOREIGN PATENT DOCUMENTS

| | | | | |
|---|---|---|---|---|
| JP | 8-317926 | * | 12/1996 | ............ G01N 29/07 |
| JP | 3642607 B2 | | 4/2005 | |
| JP | 2007007045 A | | 1/2007 | |
| JP | 2008264531 A | | 11/2008 | |
| JP | 2010082190 A | | 4/2010 | |
| JP | 2010099452 A | | 5/2010 | |
| JP | 2011092686 A | | 5/2011 | |
| JP | 2012010875 A | | 1/2012 | |

OTHER PUBLICATIONS

Machine translation and a Office Action issued in connection with Corresponding JP Application No. 2014-111064 dated Apr. 25, 2017.

* cited by examiner

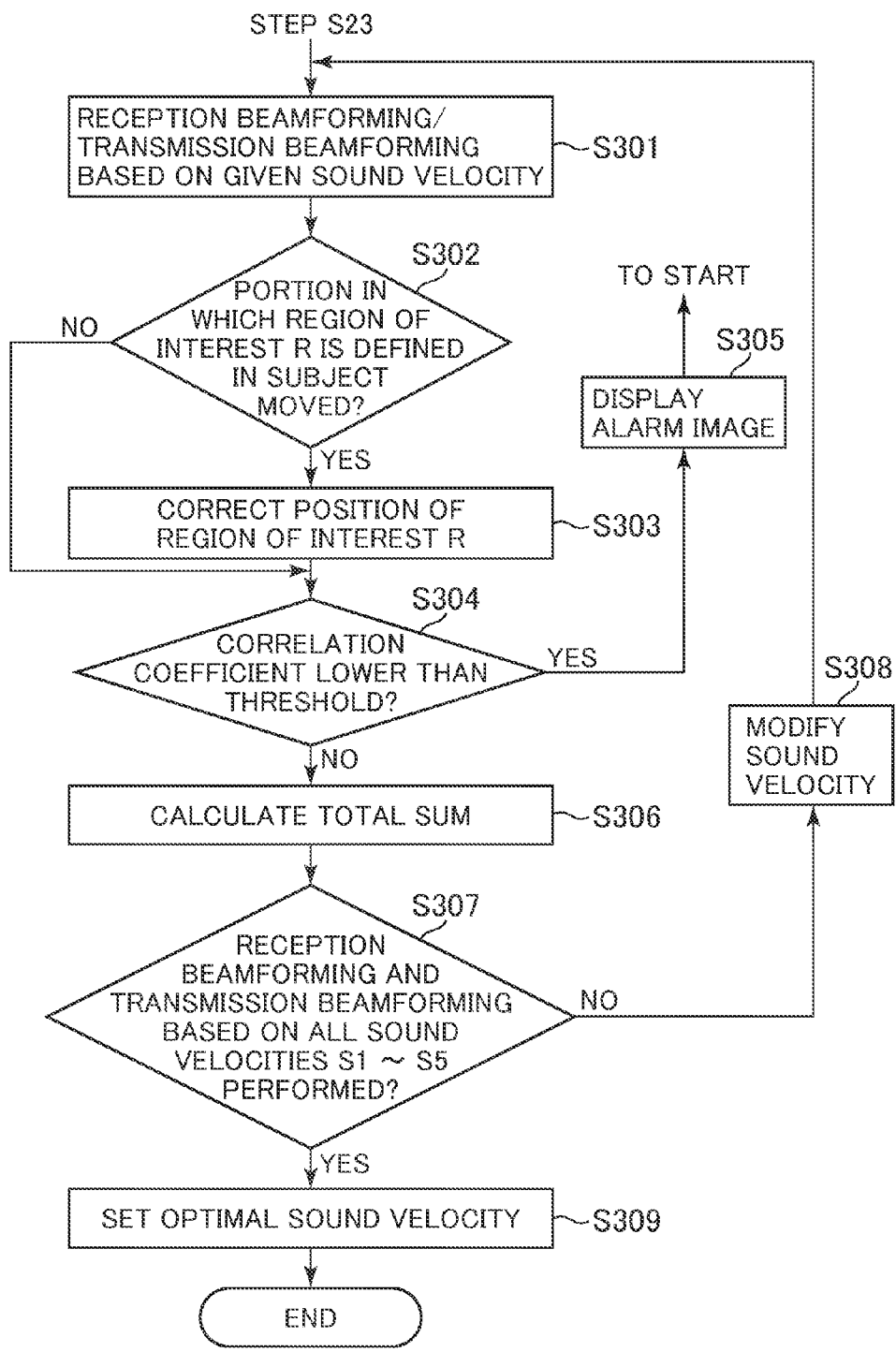

ULTRASONIC DIAGNOSTIC APPARATUS

FIELD OF THE INVENTION

Embodiments of the present invention relate to an ultrasonic diagnostic apparatus for conducting transmission/reception of ultrasound to/from a subject.

BACKGROUND

An ultrasonic diagnostic apparatus transmits ultrasound to biological tissue in a subject by an ultrasonic probe. Echo signals of the ultrasound are received by the ultrasonic probe, and an ultrasonic image based on the echo signals is produced.

The ultrasonic probe comprises a plurality of ultrasonic vibrators. Transmission/reception of ultrasound is conducted in each of the plurality of ultrasonic vibrators. An echo signal received at each ultrasonic vibrator is input to a reception beamformer. The reception beamformer applies reception beamforming to the echo signal received at each ultrasonic vibrator. The reception beamforming is phased-addition processing involving delaying the echo signals received at the ultrasonic vibrators and adding the resulting signals together.

A delay time in the reception beamforming is defined assuming that the sound velocity of ultrasound in biological tissue has a given value. The value of the sound velocity of ultrasound in biological tissue, however, may sometimes vary from subject to subject or from region to region. Therefore, in case that the value of the sound velocity set for determining a delay time is different from an actual value of the sound velocity, a reception focus may be degraded.

Accordingly, Japanese Patent No. 3642607 discloses an ultrasonic tomography apparatus for determining a value of the sound velocity of ultrasound such that a variance of the spatial frequency for the amplitude of ultrasonic received signals is maximized, and correcting a value of the sound velocity of ultrasound set in the apparatus.

SUMMARY OF THE INVENTION

According to the technique described in Japanese Patent No. 3642607, however, in case that a structure such as a bone or a blood vessel is contained in a region subjected to analysis of the spatial frequency, comparatively low spatial frequency components corresponding to the structure are dominant. For example, in case that a structure extending in a transverse direction is contained, comparatively low spatial frequency components corresponding to the structure are dominant in a result of spatial frequency analysis in a horizontal direction. Consequently, even when the value of the sound velocity in biological tissue changes, an effect thereof on the result of spatial frequency analysis may be relatively small, causing concern that the variance in the result of spatial frequency analysis may be rather unchanged. This may prevent identification of an optimal sound velocity.

Since the spatial resolution of an ultrasonic image is higher in case that the actual sound velocity in biological tissue matches a set sound velocity set in reception beamforming than in case that the actual sound velocity does not match the set sound velocity, the intensity of a particular spatial frequency is enhanced regardless of the presence of a structure. Embodiments of the invention made for solving the aforementioned problem in one aspect is an ultrasonic diagnostic apparatus characterized in comprising: an ultrasonic probe for transmitting/receiving ultrasound to/from a subject; a reception beamformer for applying reception beamforming based on a plurality of different sound velocities to ultrasonic echo signals obtained by said ultrasonic probe; a spatial frequency analyzing section for applying spatial frequency analysis to each of data obtained by said reception beamforming based on each of said plurality of different sound velocities; and a sound-velocity setting section for setting a sound velocity corresponding to one of results of said spatial frequency analysis corresponding respectively to said plurality of different sound velocities that has a highest intensity for a given spatial frequency, as optimal sound velocity in said reception beamforming.

The invention in another aspect is an ultrasonic diagnostic apparatus characterized in that: said spatial frequency analyzing section in the invention in said one aspect comprises a decision section for performing said spatial frequency analysis for a region of interest in said subject, comparing intensities of said given spatial frequency with one another among results of said spatial frequency analysis corresponding respectively to said plurality of different sound velocities, and in case that a difference between highest and lowest intensities is smaller than a given threshold, deciding that a position of said region of interest is not suitable for determining an optimal sound velocity in said reception beamforming.

The invention in still another aspect is an ultrasonic diagnostic apparatus characterized in comprising: an ultrasonic probe for transmitting/receiving ultrasound to/from a subject; a reception beamformer for applying reception beamforming to ultrasonic echo signals obtained by said ultrasonic probe based on a given sound velocity; a spatial frequency analyzing section for performing spatial frequency analysis in a region of interest in said subject based on data obtained by said reception beamforming; and a decision section for comparing, in a result of said spatial frequency analysis, an intensity of a first spatial frequency corresponding to an obstacle hindering determination of an optimal sound velocity in said reception beamforming with an intensity of a second spatial frequency different from said first spatial frequency, and deciding whether or not said obstacle is contained in said region of interest.

According to the invention in one aspect, since a sound velocity corresponding to a result of spatial frequency analysis that has a highest intensity for the given spatial frequency is set as optimal sound velocity in the reception beamforming, an optimal sound velocity can be set regardless of the presence of a structure.

According to the invention in another aspect, intensities of the given spatial frequency are compared with one another among results of the spatial frequency analysis corresponding respectively to the plurality of different sound velocities, and in case that a difference between highest and lowest intensities is smaller than a given threshold, it is decided by the decision section that a position of the region of interest is not suitable for determining an optimal sound velocity in the reception beamforming. At that time, even when a sound velocity set in reception beamforming matches an actual sound velocity, spatial resolution in the region of interest defined at a position away from an ultrasonic beam focus is degraded as compared with spatial resolution in the proximity of the focus. In this case, even when the sound velocity in reception beamforming changes, no significant change is observed in spatial resolution in the region of interest, and hence, no significant change is observed in an intensity of the given spatial frequency. Accordingly, the decision section compares intensities of the given spatial frequency with one another among results of the spatial frequency analysis corresponding respectively to the plurality of different sound velocities, and in case that a difference between highest and lowest intensities is smaller than a given threshold, it decides that the position is not suitable for determining an optimal sound velocity in the reception beamforming; and thus, the region of interest can be defined at a suitable position.

According to the invention in still another aspect, in a result of the spatial frequency analysis, an intensity of a first spatial frequency corresponding to an obstacle hindering determination of an optimal sound velocity in the reception beamforming is compared with an intensity of a second spatial frequency different from the first spatial frequency, and whether or not the obstacle is contained in the region of interest is decided by the decision section. At that time, in case, for example, that the obstacle is contained in the region of interest, an intensity of a spatial frequency corresponding to the obstacle is enhanced relative to the intensity of the other spatial frequencies. Accordingly, the intensity of the first spatial frequency is compared with the intensity of the second spatial frequency, and whether or not the obstacle is contained in the region of interest is decided, whereby the region of interest can be defined at a position at which no obstacle is contained. Therefore, an optimal sound velocity can be set based on ultrasonic echo signals obtained from the region of interest defined at such a position.

BRIEF DESCRIPTION OF THE DRAWINGS

FIG. 17 is a flow chart showing an operation at Step S30 shown in FIG. 16.

DETAILED DESCRIPTION

Now embodiments of the present invention will be described with reference to the accompanying drawings.

Figure 1:
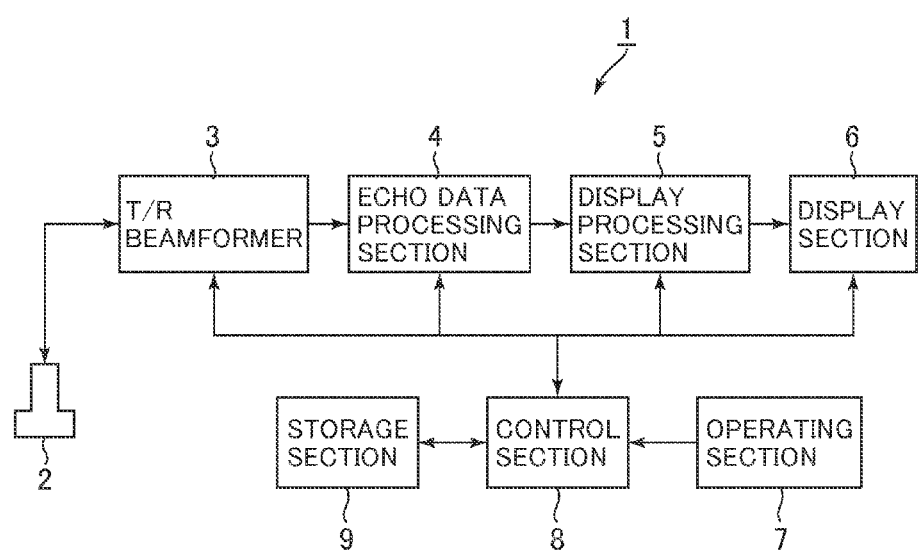
FIG. 1 is a block diagram showing a schematic configuration of an ultrasonic diagnostic apparatus representing an exemplary embodiment of the present invention.

An ultrasonic diagnostic apparatus 1 shown in FIG. 1 comprises an ultrasonic probe 2, a transmission/reception (T/R) beamformer 3, an echo data processing section 4, a display processing section 5, a display section 6, an operating section 7, a control section 8, and a storage section 9.

The ultrasonic probe 2 is configured to have a plurality of ultrasonic vibrators (not shown) arranged in an array, and ultrasound is transmitted to a subject and echo signals therefrom are received by these ultrasonic vibrators. The ultrasonic probe 2 represents an exemplary embodiment of the ultrasonic probe in the present invention.

Figure 2:
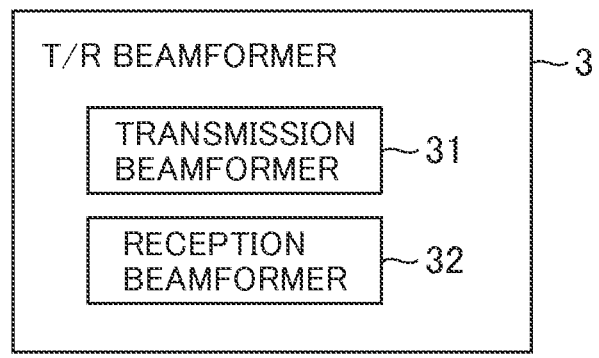
FIG. 2 is a block diagram showing a configuration of a transmission/reception beamformer.

The T/R beamformer 3 comprises a transmission beamformer 31 and a reception beamformer 32, as shown in FIG. 2. The transmission beamformer 31 drives the ultrasonic probe 2 to transmit ultrasound having given transmission parameters based on control signals from the control section 8. For example, the transmission beamformer 31 performs transmission beamforming using a delay time defined based on a given set sound velocity. The given set sound velocity includes a plurality of different sound velocities. The transmission beamformer 31 represents an exemplary embodiment of the transmission beamformer in the present invention.

The reception beamformer 32 applies reception beamforming (phased-addition processing) based on control signals from the control section 8 using a delay time defined according to the given set sound velocity to ultrasonic echo signals obtained at the ultrasonic probe 2. The given set sound velocity includes a plurality of different sound velocities. The reception beamformer 32 represents an exemplary embodiment of the reception beamformer in the present invention.

The echo data processing section 4 applies signal processing for producing an ultrasonic image and the like to echo data output from the T/R beamformer 3. For example, the echo data processing section 4 applies B-mode processing such as logarithm compression processing and envelope detection processing to the echo data output from the T/R beamformer 3 to create B-mode data.

The display processing section 5 scan-converts data output from the echo data processing section 4 by a scan converter to create ultrasonic image data, and displays an ultrasonic image based on the ultrasonic image data in the display section 6. For example, the display processing section 5 scan-converts the B-mode data by the scan converter to create B-mode image data, and displays a B-mode image based on the B-mode image data on the display section 6. The data before being scan-converted by the scan converter will be referred to as raw data hereinbelow.

The display section 6 is an LCD (Liquid Crystal Display), an organic EL (Electro-Luminescence) display, or the like. The operating section 7 is configured to comprise a keyboard for allowing an operator to input a command and/or information, a pointing device such as a trackball, and the like, although not particularly shown.

The control section 8 is a processor such as a CPU (Central Processing Unit). The control section 8 loads thereon a program stored in the storage section 9 and controls several sections in the ultrasonic diagnostic apparatus 1. For example, the control section 8 loads thereon a program stored in the storage section 9 and executes functions of the T/R beamformer 3, echo data processing section 4, and display processing section 5 by the loaded program.

The control section 8 may execute all of the functions of the T/R beamformer 3, all of the functions of the echo data processing section 4, and all of the functions of the display processing section 5 by the program, or execute only some of the functions by the program. In case that the control section 8 executes only some of the functions, the remaining functions may be executed by hardware such as circuitry.

It should be noted that the functions of the T/R beamformer 3, echo data processing section 4, and display processing section 5 may be implemented by hardware such as circuitry.

Figure 3:
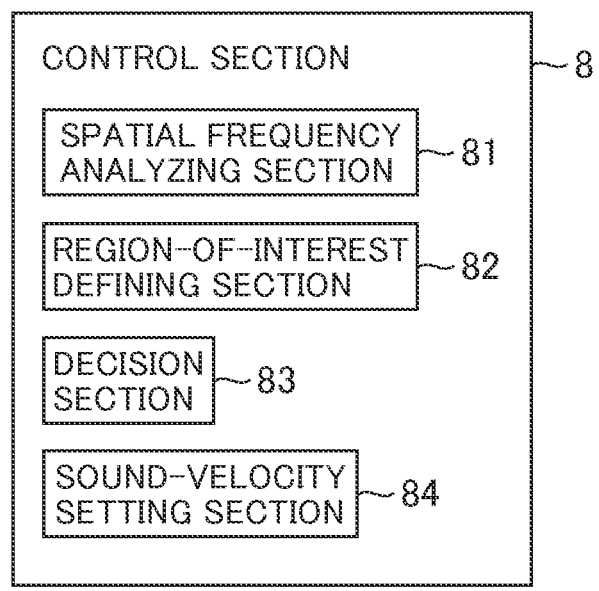
FIG. 3 is a block diagram showing some of functions of a control section.

The control section 8 also loads thereon a program stored in the storage section 9 and executes functions of a spatial frequency analyzing section 81, a region-of-interest defining section 82, a decision section 83, and a sound-velocity setting section 84 shown in FIG. 3 by the program.

The spatial frequency analyzing section 81 applies spatial frequency analysis to the data output from the reception beamformer 32. The spatial frequency analyzing section 81 performs spatial frequency analysis based on each of data obtained by the reception beamforming according to each of the plurality of different sound velocities in a region of interest, which will be discussed later.

The region-of-interest defining section 82 defines a region of interest in a B-mode image displayed in the display section 6. The region-of-interest defining section 82 represents an exemplary embodiment of the region-of-interest defining section in the present invention.

The decision section 83 decides whether a position of the region of interest is suitable or not. Details thereof will be discussed later. The decision section 83 represents an exemplary embodiment of the decision section in the present invention.

The sound-velocity setting section 84 sets an optimal sound velocity in the reception beamforming. The sound-velocity setting section 84 may set an optimal sound velocity in the transmission beamforming as well. The optimal sound velocity as used herein refers to a sound velocity giving the highest spatial resolution of an ultrasonic image. The sound-velocity setting section 84 sets a sound velocity corresponding to one of results of the spatial frequency analysis corresponding respectively to the plurality of different sound velocities that has a highest intensity for a given spatial frequency, as the optimal sound velocity. Details thereof will be discussed later.

The storage section 9 is an HDD (Hard Disk Drive), and/or a semiconductor memory such as a RAM (Random Access Memory) and/or a ROM (Read-Only Memory).

Figure 4:
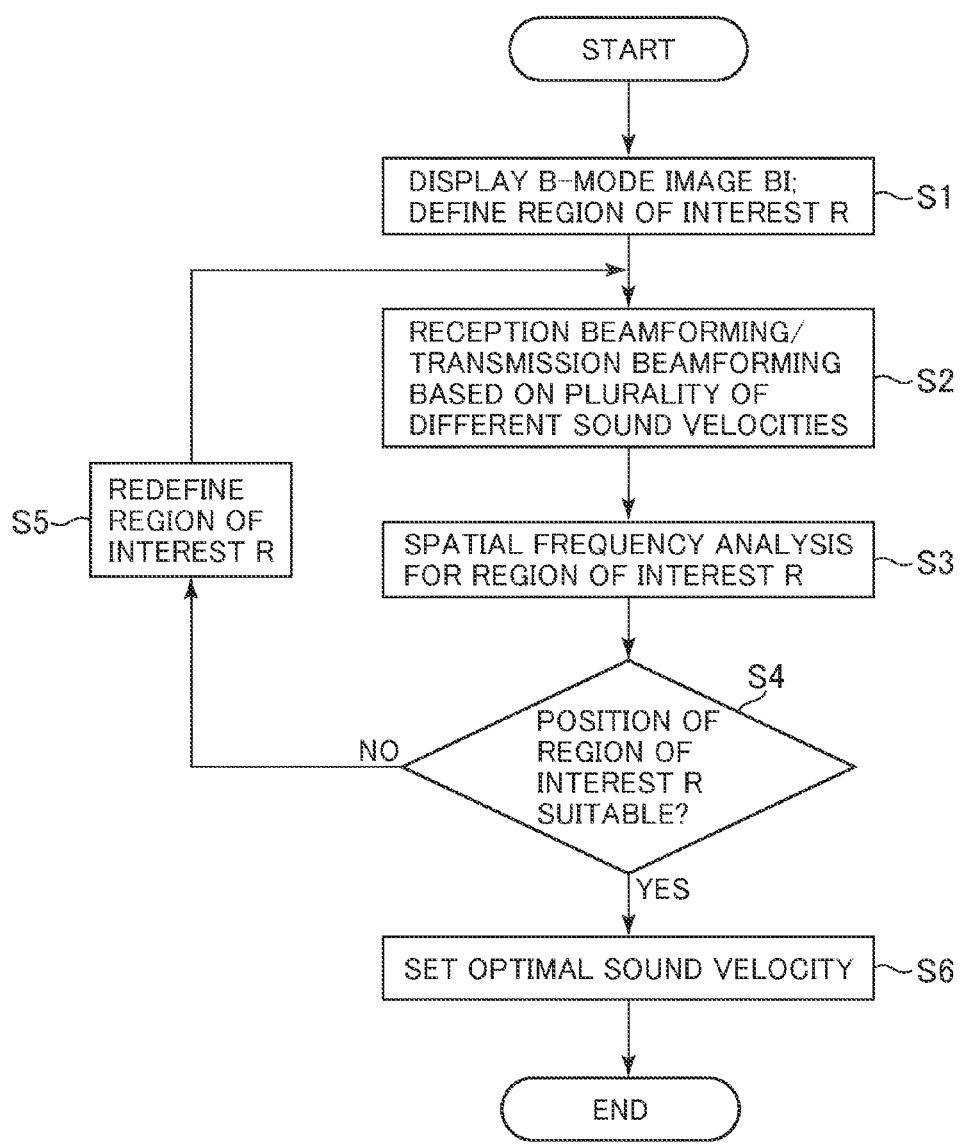
FIG. 4 is a flow chart showing an operation in the first embodiment.

Next, an operation of the ultrasonic diagnostic apparatus 1 in the present embodiment will be described based on a flow chart in FIG. 4. Here, setting of an optimal sound velocity in the reception beamforming and transmission beamforming will be described.

Figure 5:
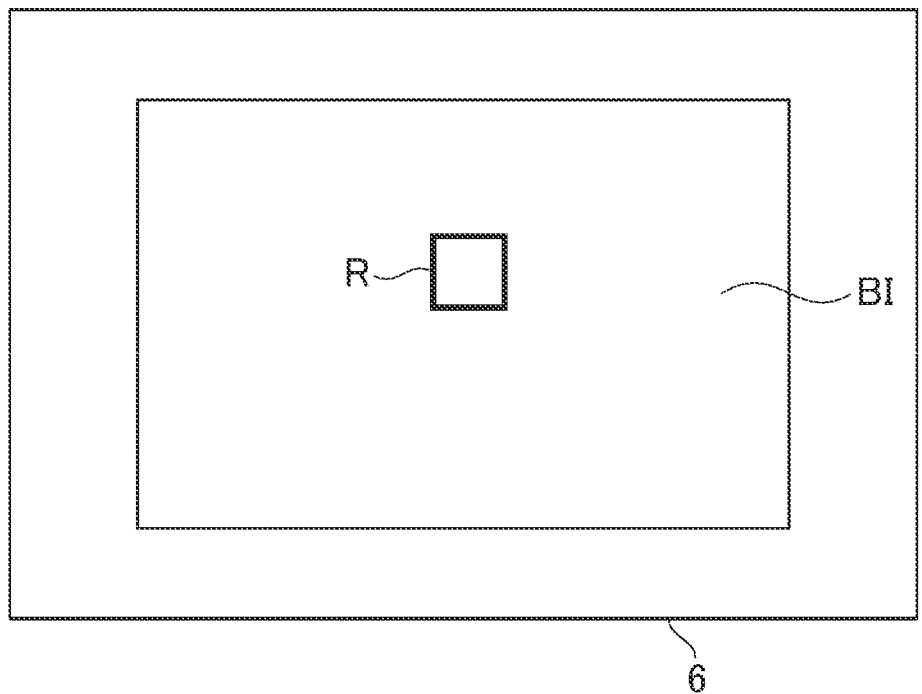
FIG. 5 is a diagram showing a display section in which a region of interest is defined in a B-mode image.

First, at Step S1, an operator starts transmission/reception of ultrasound from/to the ultrasonic probe 2 to/from a subject, and displays a B-mode image BI based on the ultrasonic echo signals, as shown in FIG. 5. At Step S1, a sound velocity in transmission beamforming and reception beamforming in displaying the B-mode image BI is a given preset sound velocity.

The operator defines a region of interest R in the B-mode image BI. In particular, when the operator makes an input for defining the region of interest R at the operating section 7, the region-of-interest defining section 82 defines the region of interest R. The operator defines the region of interest R so that it contains an ultrasonic beam focus.

It should be noted that the definition of the region of interest R is not limited to being made by an operator. The region of interest R may be defined by the region-of-interest defining section 82 at a predetermined position. In this case, again, the region of interest R is defined to contain the ultrasonic beam focus. In case that the region of interest R is thus automatically defined by the region-of-interest defining section 82, the region of interest R does not need to be displayed in the display section 6.

Next, at Step S2, the reception beamformer 32 applies reception beamforming to echo signals obtained at the ultrasonic probe 2 based on a plurality of different sound velocities. For example, the reception beamformer 32 performs reception beamforming based on each of sound velocities S1, S2, S3, S4, S5.

Moreover, at Step S2, the transmission beamformer 31 may perform transmission beamforming based on a plurality of different sound velocities. For example, the transmission beamformer 31 may perform transmission beamforming based on each of the sound velocities S1, S2, S3, S4, S5.

While the sound velocities used in the reception beamforming and transmission beamforming include five sound velocities S1-S5 here, the number of sound velocities used in the reception beamforming and transmission beamforming may be more than or less than five.

Next, at Step S3, the spatial frequency analyzing section 81 applies spatial frequency analysis to data output from the reception beamformer 32. The spatial frequency analysis is performed for the region of interest R. More specifically, the spatial frequency analyzing section 81 applies spatial frequency analysis for the region of interest R to each of data D1 obtained by reception beamforming based on the sound velocity S1, data D2 obtained by reception beamforming based on the sound velocity S2, data D3 obtained by reception beamforming based on the sound velocity S3, data D4 obtained by reception beamforming based on the sound velocity S4, and data D5 obtained by reception beamforming based on the sound velocity S5.

The spatial frequency analyzing section 81 may apply spatial frequency analysis to raw data output from the reception beamformer 32, or to image data (B-mode image data) obtained after scan-converting the raw data by the display processing section 5. That is, the spatial frequency analyzing section 81 may apply spatial frequency analysis to data at least after reception beamforming.

Figure 6:
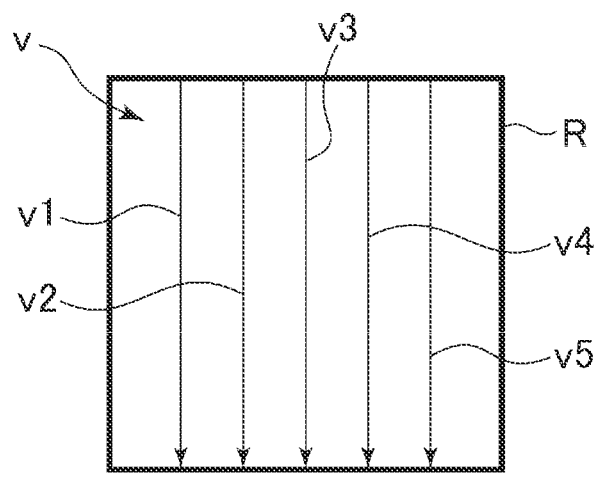
FIG. 6 is a diagram explaining FFT in an ultrasound acoustic-line direction.
Figure 7:
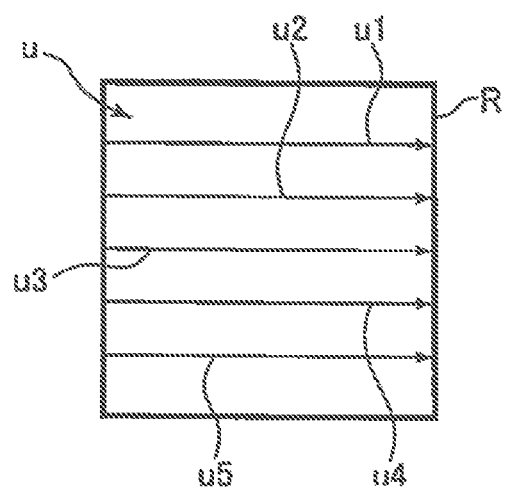
FIG. 7 is a diagram explaining FFT in a direction orthogonal to the ultrasound acoustic-line direction.

The spatial frequency analysis is two-dimensional FFT (Fast Fourier Transform), for example. In the region of interest R, the spatial frequency analyzing section 81 applies FFT, for example, in an ultrasound acoustic-line direction v as shown in FIG. 6, and FFT in a direction u orthogonal to the acoustic-line direction v as shown in FIG. 7. This gives a result of FFT in the ultrasound acoustic-line direction v and a result of FFT in the direction u orthogonal to the acoustic-line direction v for each of the data D1-D5. The ultrasound acoustic-line direction v represents an exemplary embodiment of the first direction in the present invention, and the direction u orthogonal to the acoustic-line direction v represents an exemplary embodiment of the second direction in the present invention.

Now we represent results of spatial frequency analysis on the data D1 as Re1A, Re1B, results of spatial frequency analysis on the data D2 as Re2A, Re2B, results of spatial frequency analysis on the data D3 as Re3A, Re3B, results of spatial frequency analysis on the data D4 as Re4A, Re4B, and results of spatial frequency analysis on the data D5 as Re5A, Re5B. The results Re1A-Re5A of spatial frequency analysis are results of FFT in the ultrasound acoustic-line direction v. The results Re1B-Re5B of spatial frequency analysis are results of FFT in the direction u orthogonal to the acoustic-line direction v.

FFT in the ultrasound acoustic-line direction v is performed a plurality of number of times (v1-v5 in FIG. 6). The results Re1A-Re5A of spatial frequency analysis are each obtained by averaging results of FFT for the plurality of number of times. Similarly, FFT in the direction u orthogonal to the acoustic-line direction v is performed a plurality of number of times (u1-u5 in FIG. 7). The results Re1B-Re5B of spatial frequency analysis are also each obtained by averaging results of FFT for the plurality of number of times.

Next, at Step S4, the decision section 83 decides whether a position of the region of interest R is suitable or not. The phrase that a position of the region of interest R is suitable as used herein refers to a condition that the region of interest R is defined to contain an ultrasonic beam focus, and is defined at a position at which the B-mode image has the spatial resolution required to determine an optimal sound velocity. When the region of interest R is defined at a position away from the ultrasonic beam focus and the spatial resolution of the B-mode image lowers, a change in sound velocity in reception beamforming and transmission beamforming causes no significant change in spatial resolution of the B-mode image. In this case, the sound velocity cannot be optimally set. Accordingly, whether the position of the region of interest R is suitable or not is decided at Step S4.

Even though the operator believes he/she has defined the region of interest R to include an ultrasonic beam focus at Step S1 described above, the region of interest R may be sometimes actually defined at a position not containing the focus. Accordingly, the processing at Step S4 is required.

Now decision made by the decision section 83 will be particularly described. The decision section 83 compares intensities of a given spatial frequency f with one another among the results Re1A-Re5A of spatial frequency analysis. The decision section 83 also compares intensities of the given spatial frequency f with one another among the results Re1B-Re5B of spatial frequency analysis. The intensity of a spatial frequency is an amplitude in a spatial frequency spectrum obtained by spatial frequency analysis.

Figure 8:
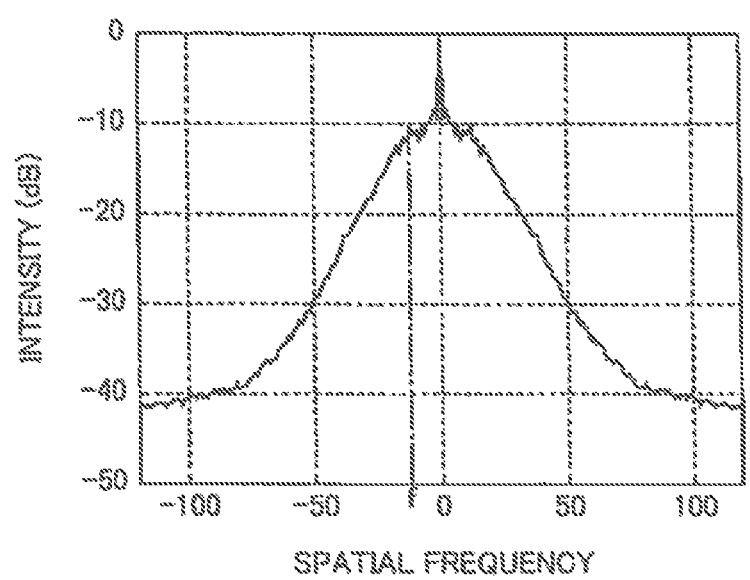
FIG. 8 is a diagram showing an exemplary result of analysis on spatial frequency.

Now the given spatial frequency will be described based on FIG. 8. FIG. 8 represents an exemplary result Re of spatial frequency analysis. In FIG. 8, a given spatial frequency f in the exemplary result Re of spatial frequency analysis is shown. The spatial frequency f is a spatial frequency that is dominant (has a high intensity) in a speckle pattern of a B-mode image in case that a set sound velocity in reception beamforming matches the sound velocity of biological tissue of a subject to/from which ultrasound is transmitted/received. The speckle pattern in the B-mode image is determined according to properties of the biological tissue and parameters affecting the spatial resolution of the B-mode image.

The parameters affecting the spatial resolution of the B-mode image include a ultrasound transmission frequency, an ultrasound acoustic line density, and a factor in scan conversion by the display processing section 5 (how many acoustic lines are to be assigned to a pixel in an ultrasonic image).

While a given spatial frequency f in one of results of spatial frequency analysis is shown in FIG. 8, comparison of intensities of the given spatial frequency f with one another by the decision section 83 is performed for the results Re1A-Re5A of spatial frequency analysis and results Re1B-Re5B of spatial frequency analysis.

Moreover, a plurality of the given spatial frequencies f may be present.

The decision section 83 compares intensities of the given spatial frequency f with one another among the results Re1A-Re5A of spatial frequency analysis, and decides whether a difference between highest and lowest intensities is smaller than a given threshold or not. The decision section 83 also compares intensities of the given spatial frequency f with one another among the results of spatial frequency analysis Re1B-Re5B, and decides whether a difference between highest and lowest intensities is smaller than the given threshold or not. In case that the difference between highest and lowest intensities is equal to or greater than the given threshold in any one of the results of decision, the decision section 83 decides that the position of the region of interest R is suitable for determining an optimal sound velocity in the reception beamforming.

Figure 9:
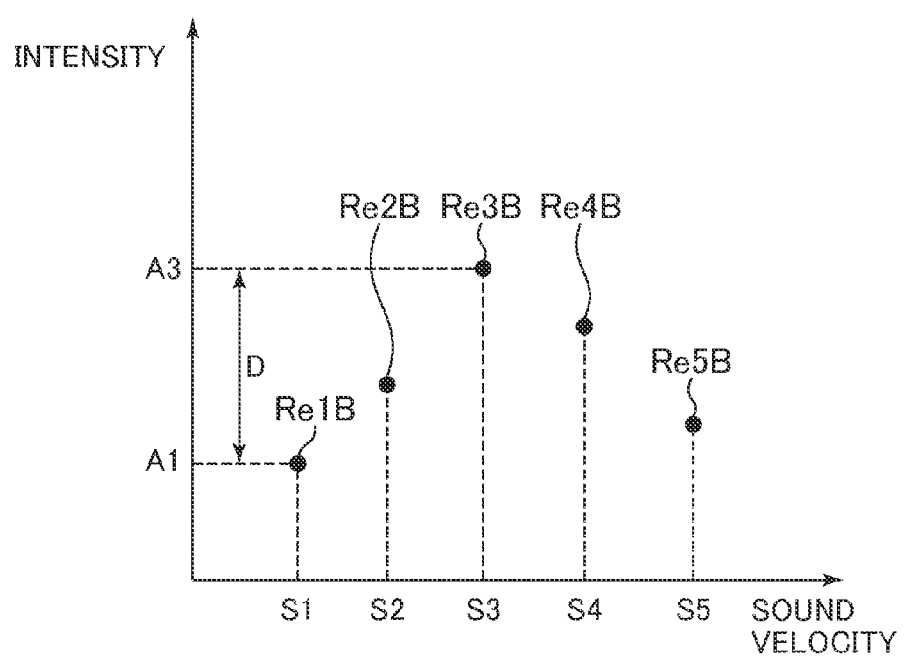
FIG. 9 is a diagram showing intensities of a particular spatial frequency in results of spatial frequency analysis corresponding to sound velocities.

For example, assume that an intensity A1 of the given spatial frequency f in the result Re1B of the spatial frequency analysis corresponding to the sound velocity S1 is lowest and an intensity A3 of the given spatial frequency f in the result Re3B of the spatial frequency analysis corresponding to the sound velocity S3 is highest, as shown in FIG. 9. In this case, the decision section 83 decides that the position of the region of interest R is suitable for determining an optimal sound velocity in the reception beamforming ("YES" at Step S4) when a difference D between the intensity A1 and intensity A3 is equal to or greater than a given threshold Dth. The given threshold Dth is set to such a value that, as the sound velocity in reception beamforming and transmission beamforming changes, the resolution of a B-mode image noticeably changes to a degree that allows an optimal sound velocity to be set.

On the other hand, the decision section 83 decides that the position of the region of interest R is not suitable when the difference between highest and lowest intensities is smaller than the given threshold in the result of decision ("NO" at Step S4).

In case that the position of the region of interest R is decided not to be suitable for determining an optimal sound velocity in the reception beamforming at Step S4, flow proceeds to processing at Step S5. At Step S5, the operator redefines the region of interest R. In particular, the decision that the position of the region of interest R is not suitable is first notified to the operator. For example, the display processing section 5 displays a message indicating that the position of the region of interest R is not suitable in the display section 6. Alternatively, a message may be displayed for prompting the operator to redefine the region of interest R because the position of the region of interest R is not suitable. Moreover, the control section 8 may generate an alarm sound in place of the message. In this case, the display processing section 5 and control section 8 perform the function of the notifying section for notifying that the position of the region of interest is not suitable.

Upon the notification, the operator redefines the region of interest R. In the redefinition, the operator changes the position of the region of interest R. Once the region of interest R has been redefined at Step S5, flow goes back to processing at Step S2.

On the other hand, in case that the position of the region of interest R is decided to be suitable for determining an optimal sound velocity in the reception beamforming at Step S4, flow proceeds to processing at Step S6. At Step S6, the sound-velocity setting section 84 sets an optimal sound velocity. The optimal sound velocity is a sound velocity used in the reception beamforming and transmission beamforming.

The sound-velocity setting section 84 sets a sound velocity corresponding to one of the results Re1A-Re5A of spatial frequency analysis and results Re1B-Re5B of spatial frequency analysis that has a highest intensity for the given spatial frequency f, as optimal sound velocity. For example, in case that the intensity A3 of the given spatial frequency f is highest in the result Re3B of spatial frequency analysis as shown in FIG. 9, the sound-velocity setting section 84 sets a sound velocity S3 corresponding to the result Re3B of spatial frequency analysis as optimal sound velocity.

It should be noted that in case that the intensity of the given spatial frequency f is highest in the results Re1A-Re5A of spatial frequency analysis and results Re1B-Re5B of spatial frequency analysis, and at the same time, a difference between highest and lowest intensities of the given spatial frequency f is equal to or greater than the given threshold, the sound-velocity setting section 84 sets a sound velocity corresponding to the result of spatial frequency analysis that has a highest intensity for the given spatial frequency f as optimal sound velocity. This will be particularly described based on FIG. 10.

Figure 10:
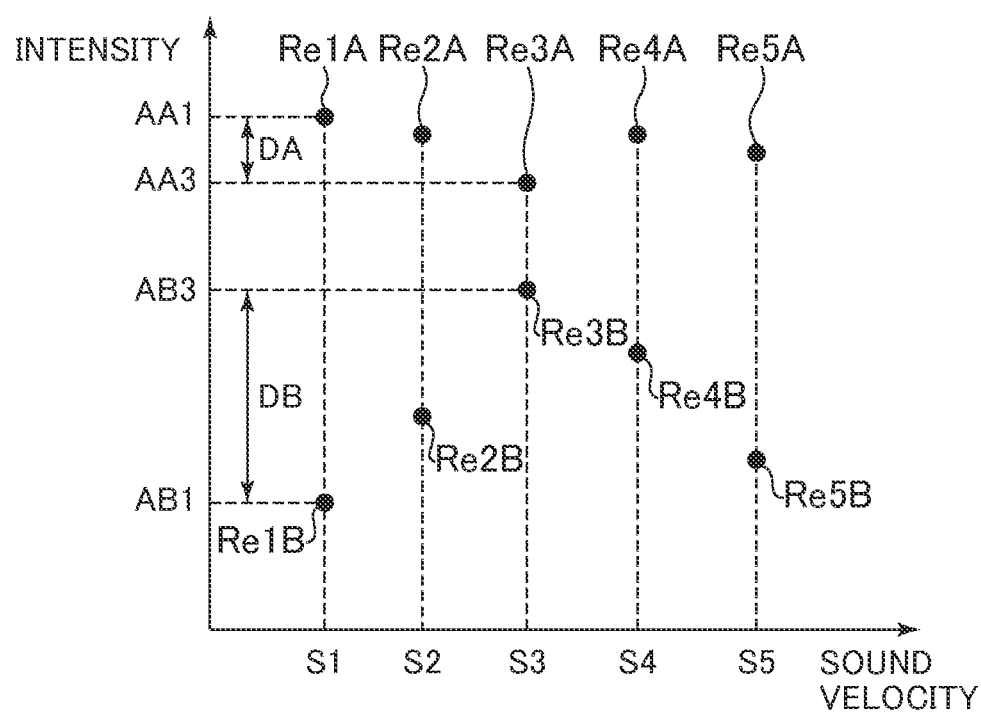
FIG. 10 is a diagram showing intensities of a particular spatial frequency in results of spatial frequency analysis corresponding to sound velocities.

Assume that among the intensities of the given spatial frequency f in the results Re1A-Re5A of spatial frequency analysis, the intensity AA1 of the given spatial frequency f in the result Re1A of spatial frequency analysis is highest, and the intensity AA3 of the given spatial frequency f in the result Re3A of spatial frequency analysis is lowest, as shown in FIG. 10. Similarly, assume that among the intensities of the given spatial frequency f in the results Re1B-Re5B of spatial frequency analysis, the intensity AB3 of the given spatial frequency f in the result Re3B of spatial frequency analysis is highest, and the intensity AB1 of the given spatial frequency f in the result Re1B of spatial frequency analysis is lowest. In case that a difference DA between the intensity AB3 and intensity AB1 is equal to or greater than the given threshold Dth, and a difference DB between the intensity AA1 and intensity AA3 is smaller than the given threshold Dth, the sound-velocity setting section 84 sets the sound velocity S3 corresponding to the result Re3B of spatial frequency analysis as optimal sound velocity.

After the optimal sound velocity has been set as described above, reception beamforming and transmission beamforming are performed based on the optimal sound velocity. Then, a B-mode image based on data obtained by reception beamforming based on the optimal sound velocity is displayed.

According to the present embodiment, since a sound velocity corresponding to a result of spatial frequency analysis that has a highest intensity for the given spatial frequency f is set as optimal sound velocity in the reception beamforming and transmission beamforming, an optimal sound velocity can be set regardless of the presence of a structure in the region of interest R. This will be particularly described based on FIG. 11.

Figure 11:
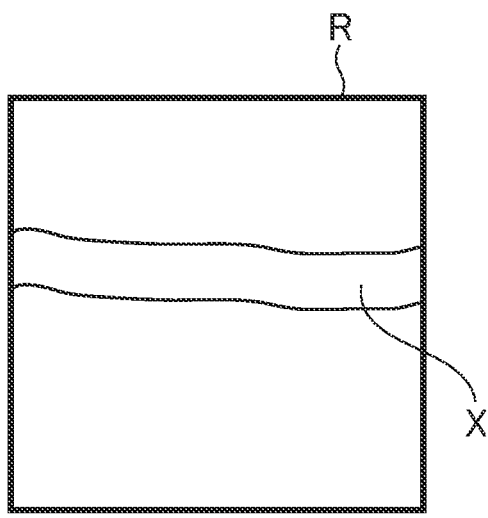
FIG. 11 is a diagram showing a region of interest in which a structure extending in the direction orthogonal to the ultrasound acoustic-line direction is present.

Referring to FIG. 11, a structure X, such as a blood vessel or a bone, is present in the region of interest R. The structure X extends in the direction u orthogonal to the ultrasound acoustic-line direction v. In the region of interest R in which such a structure X is present, the intensity of a spatial frequency with low frequency component corresponding to the structure X is higher in the results Re1B-Re5B of spatial frequency analysis as compared with that in a region of interest in which the structure X is not present. However, regardless of whether the structure X is present in the region of interest R or not, there exists a result of spatial frequency analysis that has a highest intensity for the given spatial frequency f among the results Re1B-Re5B of spatial frequency analysis. Therefore, according to the present embodiment as described above, an optimal sound velocity can be set regardless of the presence of a structure in the region of interest R.

Figure 12:
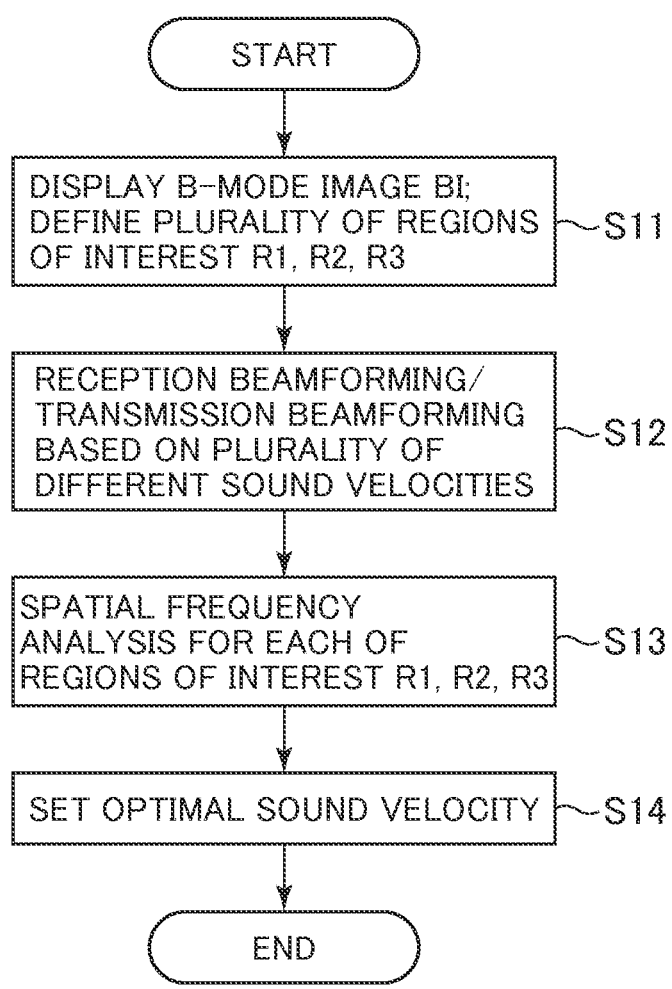
FIG. 12 is a flow chart showing an operation in a variation of the first embodiment.
Figure 13:
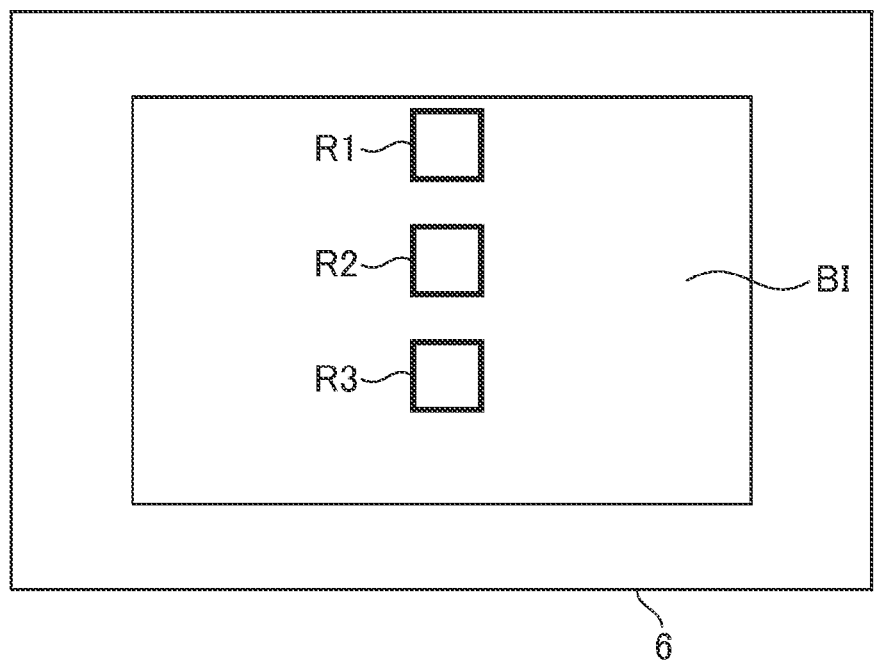
FIG. 13 is a diagram showing a display section in which a plurality of regions of interest are defined in a B-mode image.

Next, a variation of the first embodiment will be described based on a flow chart in FIG. 12. First, at Step S11, a B-mode image BI is displayed, as in Step S1 described above. Upon display of the B-mode image BI, an operator makes an input for defining a plurality of regions of interest R1, R2, R3 at the operating section 7. This input causes the region-of-interest defining section 82 to define the regions of interest R1, R2, R3 in the B-mode image BI, as shown in FIG. 13.

In this variation, again, the regions of interest R1, R2, R3 may be automatically defined by the region-of-interest defining section 82.

Next, at Step S12, reception beamforming and transmission beamforming are performed based on each of the sound velocities S1, S2, S3, S4, S5, as in Step S2 described above.

Next, at Step S13, the spatial frequency analyzing section 81 applies spatial frequency analysis to each of the data D1-D5, as in Step S13 described above, for each of the regions of interest R1, R2, R3.

Next, at Step S14, the sound-velocity setting section 84 sets an optimal sound velocity. Now this will be particularly described. The sound-velocity setting section 84 compares intensities of the given spatial frequency f with one another among the results Re1A-Re5A of spatial frequency analysis in the region of interest R1. Similarly, the sound-velocity setting section 84 compares intensities of the given spatial frequency f with one another among the results Re1A-Re5A of spatial frequency analysis for each of the regions of interest R2, R3.

Moreover, the sound-velocity setting section 84 compares intensities of the given spatial frequency f with one another among the results Re1B-Re5B of spatial frequency analysis in the region of interest R1. Similarly, the sound-velocity setting section 84 compares intensities of the given spatial frequency f with one another among the results Re1B-Re5B of spatial frequency analysis for each of the regions of interest R2, R3.

The sound-velocity setting section 84 identifies a result of spatial frequency analysis that gives a largest difference between highest and lowest intensities in the result of comparison of each intensity of the given spatial frequency f, and sets a sound velocity corresponding to the result of spatial frequency analysis as optimal sound velocity. For example, in case that a largest difference is found for the region of interest R2 between the intensity A3 of the given spatial frequency f in the result Re3B of spatial frequency analysis and the intensity A1 of the given spatial frequency f in the result Re1B of spatial frequency analysis, the sound-velocity setting section 84 sets the sound velocity S3 corresponding to the result Re3B of spatial frequency analysis in the region of interest R2 as optimal sound velocity.

Figure 14:
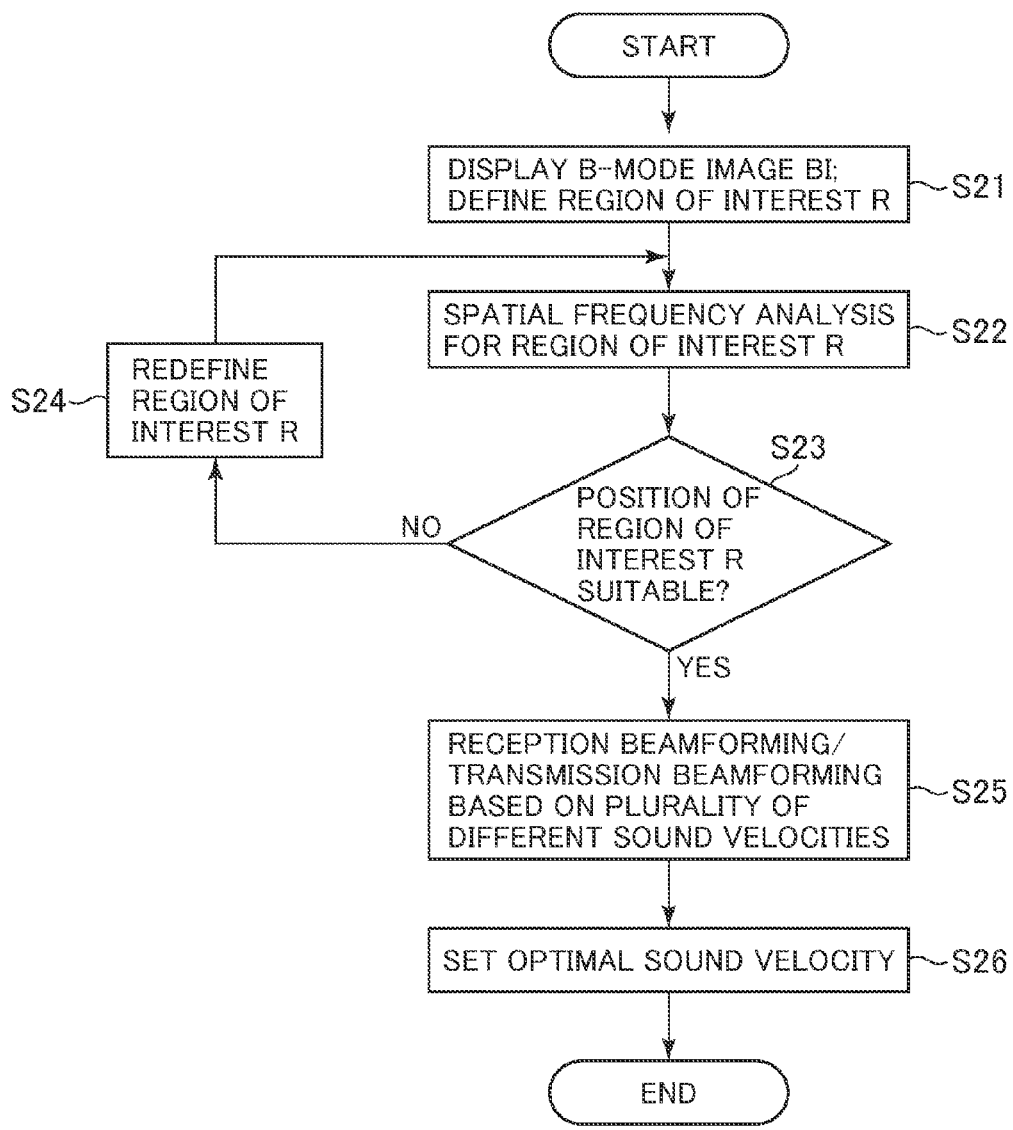
FIG. 14 is a flow chart showing an operation in a second embodiment.

Next, a second embodiment will be described. Since the basic configuration of the ultrasonic diagnostic apparatus in the second embodiment is similar to that in the first embodiment, an operation thereof will be described hereinbelow based on a flow chart in FIG. 14.

First, at Step S21, an operator starts transmission/reception of ultrasound to display a B-mode image BI, and defines a region of interest R, as in Step S1 described above. At Step S21, the sound velocity in transmission beamforming and reception beamforming in displaying the B-mode image BI is again a given preset sound velocity.

Next, at Step S22, the spatial frequency analyzing section 81 performs spatial frequency analysis for the region of interest R. At Step S22, the spatial frequency analyzing section 81 applies spatial frequency analysis to data D obtained by reception beamforming based on the given sound velocity. The spatial frequency analysis is again two-dimensional FFT, for example, as in the first embodiment.

Next, at Step S23, the decision section 83 decides whether a position of the region of interest R is suitable or not. The phrase that a position of the region of interest R is suitable as used herein refers to a condition that the region of interest R is defined at a position at which a structure hindering determination of an optimal sound velocity at Step S25, which will be described below, is not present within the region of interest R.

In particular, in the result of spatial frequency analysis obtained at Step S22 described above, the decision section 83 compares an intensity of a first spatial frequency f1 corresponding to a structure hindering determination of the optimal sound velocity, with an intensity of a second spatial frequency f2 different from the first spatial frequency f1 to decide whether or not the obstacle is contained in the region of interest. The structure hindering determination of the optimal sound velocity is, for example, the structure X such as a blood vessel or a bone, as shown in FIG. 11 described above. The structure X represents an exemplary embodiment of the obstacle in the present invention.

In case that the structure X extending in the direction u orthogonal to the acoustic-line direction v is a structure hindering determination of the optimal sound velocity, the first spatial frequency f1 has a low spatial frequency component corresponding to the structure X. The low spatial frequency component corresponding to the structure X is a spatial frequency component having a higher intensity when the structure X is present.

The second spatial frequency f2 is, for example, the given spatial frequency f.

As such, in case that the structure X is contained in the region of interest R, a difference or a ratio between the intensity of the first spatial frequency f1 and the intensity of the second spatial frequency f2 is increased in a result of FFT in the direction u orthogonal to the acoustic-line direction v as compared with a case in which the structure X is not contained in the region of interest R. Accordingly, the decision section 83 compares the intensity of the first spatial frequency f1 with the intensity of the second spatial frequency f2, and in case that a difference or a ratio between them is equal to or greater than the given threshold, it decides the position of the region of interest R is not suitable because the structure X is contained in the region of interest R ("NO" at Step S23).

On the other hand, in case that the difference or ratio between the intensity of the first spatial frequency f1 and the intensity of the second spatial frequency f2 is less than the given threshold, the decision section 83 decides that the position of the region of interest R is suitable because the structure X is not contained in the region of interest R ("YES" at Step S23).

In case that the position of the region of interest R is decided not to be suitable at Step S23, flow proceeds to processing at Step S24. At Step S24, the operator redefines the region of interest R, as in Step S5 described above. Once the region of interest R has been redefined, flow goes back to processing at Step S22.

On the other hand, in case that the position of the region of interest R is decided to be suitable at Step S23, flow proceeds to processing at Step S25. At Step S25, the reception beamformer 32 applies reception beamforming to echo signals obtained at the ultrasonic probe 2 based on a plurality of different sound velocities. For example, the reception beamformer 32 performs reception beamforming based on each of the sound velocities S1, S2, S3, S4, S5.

Moreover, the transmission beamformer 31 may perform transmission beamforming based on a plurality of different sound velocities at Step S2. For example, the transmission beamformer 31 may perform transmission beamforming based on each of the sound velocities S1, S2, S3, S4, S5.

It should be noted that the number of sound velocities used in the reception beamforming and transmission beamforming may be more than or less than five, as in Step S2 described above.

Next, at Step S26, the sound-velocity setting section 84 sets an optimal sound velocity. In the present embodiment, the sound-velocity setting section 84 sets the optimal sound velocity by a different technique from that in the first embodiment. Now this will be particularly described. First, the sound-velocity setting section 84 calculates a difference between B-mode image data at every pair of pixels that are adjacent to each other in the direction u orthogonal to the acoustic-line direction v in the region of interest R whose position is decided to be suitable at Step S23 described above, and calculates a total sum of absolute values of the differences in the region of interest R. The B-mode image data refers to B-mode image data obtained from data obtained by reception beamforming at Step S25 described above.

The total sum of absolute values of the differences refers to a total sum Sum1 for B-mode image data obtained from the data D1 obtained by reception beamforming based on the sound velocity S1, a total sum Sum2 for B-mode image data obtained from the data D2 obtained by reception beamforming based on the sound velocity S2, a total sum Sum3 for B-mode image data obtained from the data D3 obtained by reception beamforming based on the sound velocity S3, a total sum Sum4 for B-mode image data obtained from the data D4 obtained by reception beamforming based on the sound velocity S4, and a total sum Sum5 for B-mode image data obtained from the data D5 obtained by reception beamforming based on the sound velocity S5.

Next, the sound-velocity setting section 84 identifies a largest one of the total sums Sum1-Sum5, and sets the sound velocity corresponding to the B-mode image data that gives the largest total sum as optimal sound velocity. For example, in case that the total sum Sum3 is a largest total sum, the sound-velocity setting section 84 sets the sound velocity S3 corresponding to B-mode image data that gives the total sum Sum3 as optimal sound velocity. Once the optimal sound velocity has been set, reception beamforming and transmission beamforming are performed based on the optimal sound velocity, as in the first embodiment, and a B-mode image is displayed.

According to the present embodiment, the region of interest R may be defined at a position at which the structure X is not contained, and an optimal sound velocity can be set.

Figure 15:
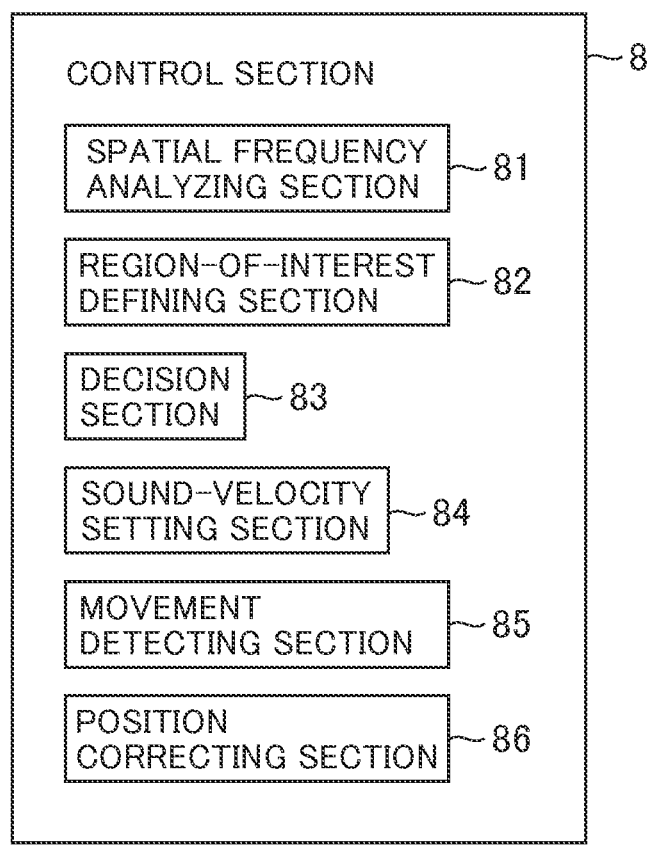
FIG. 15 is a block diagram showing some of functions of the control section in the second embodiment.

Next, a variation of the second embodiment will be described. In this variation, the control section 8 loads thereon a program stored in the storage section 9 and executes functions of the spatial frequency analyzing section 81, region-of-interest defining section 82, decision section 83, and sound-velocity setting section 84, and besides, executes functions of a movement detecting section 85 and a position correcting section 86 by the program, as shown in FIG. 15. The movement detecting section 85 represents an exemplary embodiment of the movement detecting section in the present invention. The position correcting section 86 represents an exemplary embodiment of the position correcting section in the present invention.

An operation of the variation will now be described. In the present variation, movement of a portion in which the region of interest R is defined in a subject is detected by the movement detecting section 85, and based on a detected amount of movement, the position of the region of interest R is corrected by the position correcting section 85. This will be particularly described based on a flow chart in FIG. 16. The processing at Steps S21-S24 is similar to that in the flow chart in FIG. 14. At Step S23 described above, in case that a position of the region of interest R is decided to be suitable, flow proceeds to processing at Step S30. At Step S30, the sound-velocity setting section 84 sets an optimal sound velocity. The setting of an optimal sound velocity at Step S30 will be described based on a flow chart in FIG. 17.

First, at Step S301, transmission beamforming and reception beamforming are performed based on a given sound velocity. For example, transmission beamforming and reception beamforming are performed here based on the first sound velocity S1. It should be noted that at Step S310, which will be described later, the sound velocity is sequentially modified, and reception beamforming and transmission beamforming are performed based on a sound velocity in a sequence of the sound velocity S1, and then, the sound velocity S2, sound velocity S3, sound velocity S4, and sound velocity S5 at Step S301.

Next, at Step S302, the movement detecting section 85 detects movement of a portion in which the region of interest R is defined in the subject, and decides whether or not the portion in which the region of interest R is defined has moved. The movement detected by the movement detecting section 85 indicates how much the region of interest R at a time when reception beamforming and transmission beamforming were performed based on a sound velocity set at immediately preceding Step S301 has moved in what direction with respect to the region of interest R at a time when reception beamforming and transmission beamforming were performed based on a sound velocity set at next preceding Step S301 before immediately preceding Step S301. For example, how much the region of interest R at a time when reception beamforming and transmission beamforming were performed based on the sound velocity S2 has moved in what direction with respect to the region of interest R at a time when reception beamforming and transmission beamforming were performed based on the sound velocity S1 is detected by the movement detecting section 85.

It should be noted that, in case that the sound velocity set at immediately preceding Step S301 is the sound velocity S1, no reception beamforming and transmission beamforming were performed before the reception beamforming and transmission beamforming based on the sound velocity S1. In this case, movement of the region of interest R is null.

The movement detecting section 85 calculates an amount of movement of the region of interest R based on, for example, correlation calculation on B-mode image data. In case that the region of interest R is decided to move ("YES" at Step S302), flow proceeds to processing at Step S303.

At Step S303, the position correcting section 86 moves the region of interest R based on the movement detected at Step S302 to perform position correction on the region of interest R.

After the position correction on the region of interest R has been performed at Step S303, or in case that the region of interest R is decided not to move at Step S302 ("NO" at Step S302), flow proceeds to processing at Step S304. At Step S304, the control section 8 decides whether or not a correlation coefficient, which is obtained by the correlation calculation by the movement detecting section 85 at Step S302, is lower than a given threshold.

In case that the correlation coefficient is decided to be lower than the given threshold at Step S304 ("YES" at Step S304), flow proceeds to processing at Step S305. At Step S305, the display processing section 5 displays an alarm image in the display section 6. The alarm image is an image indicating that the correlation coefficient is lower than the given threshold. The alarm image is displayed by reason that the correlation coefficient is lower than the given threshold and the amount of movement is too large. The alarm image represents an exemplary embodiment of the alarm in the present invention. The display section 6 represents an exemplary embodiment of the notifying section in the present invention.

It should be noted that an alarm sound may be output at Step S305 from a speaker, which is not shown, instead of displaying the alarm image.

Figure 16:
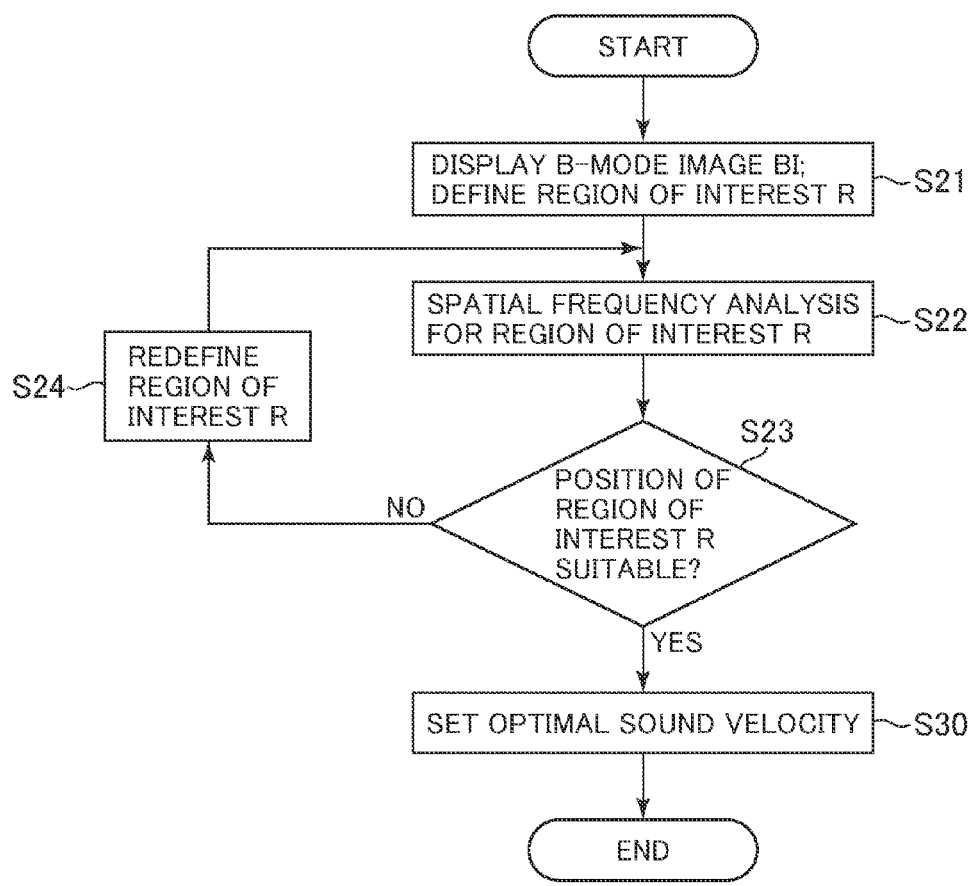
FIG. 16 is a flow chart showing an operation in a variation of the second embodiment.

Once the alarm image has been displayed (or the alarm sound has been output) at Step S305, flow goes back to "START" in the flow chart in FIG. 16. Thus, the processing flow is started again.

On the other hand, in case that the correlation coefficient is decided to be equal to or greater than the given threshold at Step S304 ("NO" at Step S304), flow proceeds to processing at Step S306. At Step S306, the sound-velocity setting section 84 calculates a difference between B-mode image data at every pair of pixels that are adjacent to each other in the direction u orthogonal to the acoustic-line direction v in the region of interest R, and calculates a total sum of absolute values of the differences in the region of interest R. The B-mode image data is obtained from the data obtained by reception beamforming based on a given sound velocity at immediately preceding Step S301.

Next, at Step S307, the control section 8 decides whether reception beamforming and transmission beamforming based on all sound velocities S1-S5 have been performed or not. In case that reception beamforming and transmission beamforming based on all sound velocities S1-S5 are decided not to be performed ("NO" at Step S307), flow proceeds to processing at Step S308.

At Step 308, the sound velocity used in reception beamforming and transmission beamforming is modified. Once the sound velocity has been modified at Step S308, flow goes back to the processing at Step S301, wherein reception beamforming and transmission beamforming based on the modified sound velocity are performed. For example, when the sound velocity used at immediately preceding Step S301 is the sound velocity S1, it is modified to the sound velocity S2 at Step S308.

On the other hand, in case that reception beamforming and transmission beamforming based on all sound velocities S1-S5 are decided to be performed at Step S307 ("YES" at Step S307), flow proceeds to processing at Step S309. At Step S309, the sound-velocity setting section 84 sets an optimal sound velocity. The sound-velocity setting section 84 identifies a largest one of the total sums Sum1-Sum5, and sets the sound velocity corresponding to the B-mode image data that gives the largest total sum as optimal sound velocity, as in Step S26 described above.

While the present invention has been described with reference to the embodiments, it will be easily recognized that the present invention may be practiced with several modifications without departing from the spirit and scope thereof. For example, setting of an optimal sound velocity may be performed at least in reception beamforming.

Moreover, the control section 8 in the first embodiment may have the movement detecting section 85 and position correcting section 86. In this case, the movement detecting section 85 detects movement of a portion in which the region of interest R, R1, R2, R3 subjected to spatial frequency analysis is defined at Step S3 in FIG. 4 and Step S13 in FIG. 12. The detection of movement is performed between data obtained by reception beamforming based on different sound velocities. For example, movement of a portion in which the region of interest R, R1, R2, R3 is defined is detected between the data D1 obtained by reception beamforming based on the sound velocity S1 and data D2 obtained by reception beamforming based on the sound velocity S2.

The position correcting section 86 moves the region of interest R, R1, R2, R3 based on the movement detected by the movement detecting section 85 to perform position correction on the region of interest R, R1, R2, R3. Spatial frequency analysis is applied for the region of interest R, R1, R2, R3 after position correction.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasonic diagnostic apparatus, comprising:
    an ultrasonic probe configured to transmit and receive ultrasound to and from a subject;
    a reception beamformer configured to apply reception beamforming based on a plurality of different sound velocities to ultrasonic echo signals obtained by said ultrasonic probe;
    a storage section configured to store a plurality of programs; and
    a processor configured to load the plurality of programs from the storage section, where the processor is further configured to:
    apply spatial frequency analysis to each of data obtained by said reception beamforming based on each of said plurality of different sound velocities; and
    compare intensities of a given spatial frequency with one another among results of said spatial frequency analysis corresponding respectively to said plurality of different sound velocities; and
    in case that a difference between highest and lowest intensities is equal to or greater than a given threshold, the processor is configured to set a sound velocity corresponding to a result of spatial frequency analysis that has said highest intensity as optimal sound velocity in said reception beamforming.

2. The ultrasonic diagnostic apparatus according to claim 1, wherein in case that a set sound velocity in said reception beamforming matches a sound velocity in biological tissue of said subject, said given spatial frequency is a spatial frequency that is dominant in a speckle pattern of an ultrasonic image, said speckle pattern being determined according to properties of said biological tissue and parameters affecting spatial resolution of an ultrasonic image.

3. The ultrasonic diagnostic apparatus according to claim 1, wherein:
    the processor is configured to perform said spatial frequency analysis for a region of interest in said subject, and
    the processor is further configured to determine that the region of interest is not suitable for determining an optimal sound velocity if the difference between highest and lowest intensities is smaller than the given threshold.

4. The ultrasonic diagnostic apparatus according to claim 3, further comprising:
    a movement detector configured to detect movement of a portion in which said region of interest is defined in said subject; and
    wherein the processor is configured to perform position correction on said region of interest based on the movement detected by said movement detector,
    wherein the processor is configured to perform spatial frequency analysis for said region of interest after position correction.

5. The ultrasonic diagnostic apparatus according to claim 3, further comprising:
    a display configured to show a result of the determination by said processor.

6. The ultrasonic diagnostic apparatus according to claim 3, wherein the processor is further configured to, in case that said region of interest is decided by said processor as not to be suitable as region of interest for determining an optimal sound velocity in said reception beamforming, define said region of interest at another position.

7. The ultrasonic diagnostic apparatus according to claim 1, wherein:
    the processor is configured to apply spatial frequency analysis to each of data obtained by reception beamforming based on each of said plurality of different sound velocities for each of a plurality of regions of interest in said subject, and
    the processor is configured to compare intensities of said given spatial frequency with one another among results of said spatial frequency analysis corresponding respectively to said plurality of different sound velocities in each of said plurality of regions of interest, identify a sound velocity corresponding to a result of spatial frequency analysis in a region of interest that gives a largest difference between highest and lowest intensities, and set said sound velocity as said optimal sound velocity.

8. The ultrasonic diagnostic apparatus according to claim 1, further comprising:
    a transmission beamformer configured to perform transmission beamforming based on a plurality of different sound velocities,
    wherein the processor is configured to set the optimal sound velocity in said reception beamforming as optimal sound velocity in said transmission beamforming.

9. The ultrasonic diagnostic apparatus according to claim 1, wherein the processor is configured to apply said spatial frequency analysis to image data obtained by scan-converting data output from said reception beamformer.

10. The ultrasonic diagnostic apparatus according to claim 1, wherein the processor is configured to apply said spatial frequency analysis to raw data output from said reception beamformer before said raw data output is scan-converted.

11. The ultrasonic diagnostic apparatus according to claim 1, wherein:
   the processor is configured to perform two-dimensional spatial frequency analysis in a first direction and a second direction different from said first direction to obtain a result of spatial frequency analysis in said first direction and a result of spatial frequency analysis in said second direction.

* * * * *